(12) United States Patent
Krieger et al.

(10) Patent No.: US 10,555,756 B2
(45) Date of Patent: Feb. 11, 2020

(54) MEDICAL DEVICES HAVING COAXIAL CANNULAE

(71) Applicant: Cook Medical Technologies LLC, Bloomington, IN (US)

(72) Inventors: Joshua Frye Krieger, Bloomington, IN (US); Melissa Lonn, Lafayette, IN (US); Jarin Kratzberg, Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 276 days.

(21) Appl. No.: 15/633,032

(22) Filed: Jun. 26, 2017

(65) Prior Publication Data

US 2017/0367730 A1   Dec. 28, 2017

Related U.S. Application Data

(60) Provisional application No. 62/354,943, filed on Jun. 27, 2016.

(51) Int. Cl.
*A61B 17/34* (2006.01)
*A61M 25/00* (2006.01)
*A61M 25/01* (2006.01)

(52) U.S. Cl.
CPC ...... *A61B 17/3421* (2013.01); *A61B 17/3439* (2013.01); *A61B 17/3462* (2013.01);
(Continued)

(58) Field of Classification Search
CPC ............ A61B 17/3421; A61B 17/3439; A61B 17/3462; A61B 2017/3433; A61B 2017/3443; A61M 25/0015; A61M 25/0043; A61M 25/0045; A61M 25/0054; A61M 25/0138; A61M 2005/3201;
(Continued)

(56) References Cited

U.S. PATENT DOCUMENTS 4,781,186 A   11/1988 Simpson et al.
5,053,004 A   10/1991 Markel et al.
(Continued)

FOREIGN PATENT DOCUMENTS

EP   0315290   5/1989
EP   0937481   8/1999
(Continued)

OTHER PUBLICATIONS

International Searching Authority, The International Search Report and Written Opinion of the International Searching Authority, dated Jul. 15, 2016, for International Application No. PCT/US2016/029670.

(Continued)

*Primary Examiner* — Bhisma Mehta
*Assistant Examiner* — James D Ponton
(74) *Attorney, Agent, or Firm* — Buchanan Van Tuinen LLC (57) ABSTRACT

The disclosure relates to medical devices comprising coaxial cannulae. A medical device includes an outer cannula and a coaxial inner cannula that is secure to the inner cannula. The circumferential wall of one of the cannulae defines a pattern of openings that extends along a spiral path about the lengthwise axis of the cannula.

20 Claims, 8 Drawing Sheets

(52) U.S. Cl.
CPC ...... *A61M 25/007* (2013.01); *A61M 25/0045* (2013.01); *A61M 25/0054* (2013.01); *A61M 25/0138* (2013.01); *A61B 2017/3433* (2013.01); *A61B 2017/3443* (2013.01); *A61M 25/0043* (2013.01); *A61M 2025/0004* (2013.01); *A61M 2025/018* (2013.01)

(58) Field of Classification Search
CPC .............. A61M 5/3291; A61M 5/3295; A61M 5/3297; A61M 2025/0175; A61M 2025/0183
See application file for complete search history.

(56) References Cited

U.S. PATENT DOCUMENTS

| | | | |
|---|---|---|---|
| 5,228,441 | A | 7/1993 | Lundquist |
| 5,284,128 | A | 2/1994 | Hart |
| 5,315,996 | A | 5/1994 | Lundquist |
| 5,322,064 | A | 6/1994 | Lundquist |
| 5,322,505 | A | 6/1994 | Krause et al. |
| 5,329,923 | A | 7/1994 | Lundquist |
| 5,425,723 | A | 6/1995 | Wang |
| 5,454,787 | A | 10/1995 | Lundquist |
| 5,460,187 | A | 10/1995 | Daigle et al. |
| 5,477,856 | A | 12/1995 | Lundquist |
| 5,507,766 | A | 4/1996 | Kugo et al. |
| 5,573,520 | A | 11/1996 | Schwartz et al. |
| 5,605,543 | A | 2/1997 | Swanson |
| 5,685,868 | A | 11/1997 | Lundquist |
| 5,741,429 | A | 4/1998 | Donadio et al. |
| 5,755,714 | A | 5/1998 | Murphy-Chutorian |
| 5,833,692 | A | 11/1998 | Cesarini et al. |
| 5,897,533 | A | 4/1999 | Glickman |
| 5,922,003 | A | 7/1999 | Anctil et al. |
| 6,059,769 | A | 5/2000 | Lunn et al. |
| 6,102,890 | A | 8/2000 | Stivland et al. |
| 6,146,373 | A | 11/2000 | Cragg et al. |
| 6,228,073 | B1 | 5/2001 | Noon et al. |
| 6,246,914 | B1 | 6/2001 | de la Rama et al. |
| 6,273,404 | B1 | 8/2001 | Holman et al. |
| 6,286,555 | B1 | 9/2001 | Paulker et al. |
| 6,350,253 | B1 | 2/2002 | Deniega et al. |
| 6,428,489 | B1 | 8/2002 | Jacobsen et al. |
| 6,611,720 | B2 | 8/2003 | Hata et al. |
| 6,623,491 | B2 | 9/2003 | Thompson |
| 6,652,508 | B2 | 11/2003 | Griffin et al. |
| 6,749,560 | B1 | 6/2004 | Konstorum et al. |
| 6,860,898 | B2 | 3/2005 | Stack et al. |
| 7,001,369 | B2 | 2/2006 | Griffin |
| 7,914,467 | B2 | 3/2011 | Layman et al. |
| 7,918,819 | B2 | 4/2011 | Karmarkar et al. |
| 7,989,042 | B2 | 8/2011 | Obara et al. |
| 8,007,434 | B2 | 8/2011 | Olson |
| 8,048,004 | B2 | 11/2011 | Davis et al. |
| 8,092,444 | B2 | 1/2012 | Lentz et al. |
| 8,105,246 | B2 | 1/2012 | Voeller et al. |
| 8,182,465 | B2 | 5/2012 | Griffin et al. |
| 8,257,279 | B2 | 9/2012 | Davis et al. |
| 8,262,563 | B2 | 9/2012 | Bakos et al. |
| 8,292,827 | B2 | 10/2012 | Musbach |
| 8,376,961 | B2 | 2/2013 | Layman et al. |
| 8,409,114 | B2 | 4/2013 | Pains |
| 8,636,716 | B2 | 1/2014 | Griffin et al. |
| 8,684,953 | B2 | 4/2014 | Cabiri |
| 8,728,010 | B2 | 5/2014 | Hirshman |
| 8,728,116 | B1 | 5/2014 | Janardhan et al. |
| 8,932,270 | B2 * | 1/2015 | O'Day .............. A61M 5/16813 604/256 |
| 2004/0097880 | A1 * | 5/2004 | Schur .................. A61M 25/007 604/164.01 |
| 2005/0125053 | A1 | 6/2005 | Yachia et al. |
| 2006/0004346 | A1 | 1/2006 | Begg |
| 2006/0100687 | A1 | 5/2006 | Fahey et al. |
| 2007/0112331 | A1 | 5/2007 | Weber et al. |
| 2007/0208405 | A1 | 9/2007 | Goodin et al. |
| 2008/0021347 | A1 | 1/2008 | Jacobsen et al. |
| 2008/0021400 | A1 | 1/2008 | Jacobsen et al. |
| 2008/0021401 | A1 | 1/2008 | Jacobsen et al. |
| 2008/0021402 | A1 | 1/2008 | Jacobsen et al. |
| 2008/0021403 | A1 | 1/2008 | Jacobsen et al. |
| 2008/0021405 | A1 | 1/2008 | Jacobsen et al. |
| 2008/0021406 | A1 | 1/2008 | Jacobsen et al. |
| 2008/0021407 | A1 | 1/2008 | Jacobsen et al. |
| 2008/0021408 | A1 | 1/2008 | Jacobsen et al. |
| 2008/0077085 | A1 | 3/2008 | Eidenschink et al. |
| 2008/0086047 | A1 | 4/2008 | McDaniel et al. |
| 2008/0097395 | A1 * | 4/2008 | Adams .............. A61M 25/0021 604/524 |
| 2008/0097398 | A1 | 4/2008 | Mitelberg et al. |
| 2008/0147001 | A1 | 6/2008 | Al-Marashi et al. |
| 2008/0294231 | A1 | 11/2008 | Aguilar et al. |
| 2009/0036832 | A1 | 2/2009 | Skujins et al. |
| 2009/0043228 | A1 | 2/2009 | Northrop et al. |
| 2009/0043283 | A1 | 2/2009 | Turnlund et al. |
| 2009/0043372 | A1 | 2/2009 | Northrop et al. |
| 2009/0177040 | A1 | 7/2009 | Lyons et al. |
| 2009/0192584 | A1 | 7/2009 | Gerdts et al. |
| 2010/0036364 | A1 | 2/2010 | Wubbeling |
| 2010/0069882 | A1 | 3/2010 | Jennings et al. |
| 2010/0087849 | A1 | 4/2010 | Griffin et al. |
| 2010/0145308 | A1 | 6/2010 | Layman et al. |
| 2011/0022069 | A1 | 1/2011 | Mitusina |
| 2011/0160834 | A1 * | 6/2011 | Aggerholm ............. A61F 2/958 623/1.11 |
| 2011/0251519 | A1 | 10/2011 | Romoscanu |
| 2011/0276034 | A1 | 11/2011 | Tomarelli et al. |
| 2012/0053419 | A1 | 3/2012 | Bloom |
| 2012/0157935 | A1 | 6/2012 | Wuebbeling et al. |
| 2012/0265229 | A1 | 10/2012 | Rottenberg et al. |
| 2013/0046285 | A1 | 2/2013 | Griffin et al. |
| 2013/0072904 | A1 | 3/2013 | Musbach et al. |
| 2013/0123768 | A1 | 5/2013 | Harlan |
| 2013/0274711 | A1 | 10/2013 | O'Day |
| 2013/0296718 | A1 | 11/2013 | Ranganathan et al. |
| 2013/0304035 | A1 | 11/2013 | Cabiri |
| 2014/0031843 | A1 | 1/2014 | Rottenberg et al. |
| 2014/0053940 | A1 | 2/2014 | Konstorum et al. |
| 2014/0081134 | A1 * | 3/2014 | Fortson ............... A61M 25/003 600/435 |
| 2014/0121590 | A1 | 5/2014 | Degen |
| 2015/0051583 | A1 * | 2/2015 | Horvath ............ A61M 25/0015 604/508 |
| 2015/0342580 | A1 | 12/2015 | Clancy |
| 2015/0374929 | A1 * | 12/2015 | Hyde .................. A61M 5/3294 604/191 |

FOREIGN PATENT DOCUMENTS

| | | |
|---|---|---|
| EP | 1656963 | 5/2006 |
| EP | 2364746 | 9/2011 |
| EP | 2762189 | 8/2014 |
| WO | WO199011313 | 3/1999 |
| WO | WO2002055146 | 7/2002 |
| WO | WO2011/008538 | 1/2011 |
| WO | WO2011008538 | 1/2011 |
| WO | WO2016176393 | 11/2016 |

OTHER PUBLICATIONS

International Searching Authority, International Search Report and Written Opinion for International Application No. PCT/US2016/029661, dated Jul. 27, 2016.

European Patent Office, Extended European Search Report for Application No. EP17178169, dated Nov. 13, 2017, pp. 1 through 8.

European Patent Office "Examination Report" for European application No. 17178169.3, dated Aug. 7, 2019, pp. 1-6.

* cited by examiner

MEDICAL DEVICES HAVING COAXIAL CANNULAE

FIELD

The disclosure relates generally to the field of medical devices. More particularly, the disclosure relates to the fields of medical devices having coaxial cannulae and methods of making medical devices that include coaxial cannulae.

BACKGROUND

Medical devices used in the delivery of treatment at a location within a body vessel require both pushability and flexibility. Development of medical devices that provide these desirable characteristics continues.

BRIEF SUMMARY OF SELECTED EXAMPLES

Several medical devices are described and illustrated herein. An example medical device comprises an inner cannula disposed within and secured to an outer cannula. The outer cannula defines a pattern of openings along a portion of the axial length of the outer cannula.

Another example medical device comprises an outer cannula having a lengthwise axis and an outer cannula circumferential wall extending between an outer cannula proximal end and an outer cannula distal end and defining an outer cannula interior lumen, the outer cannula circumferential wall defining a pattern of openings extending along a spiral path about the lengthwise axis; and an inner cannula disposed within outer cannula interior lumen and secured to the outer cannula, the inner cannula having an inner cannula circumferential wall extending between an inner cannula proximal end and an inner cannula distal end and defining an inner cannula interior lumen.

Another example medical device comprises an outer cannula having an outer cannula lengthwise axis and an outer cannula circumferential wall extending between an outer cannula proximal end and an outer cannula distal end, the outer cannula circumferential wall defining an outer cannula interior lumen and a first side port opening extending through the outer cannula circumferential wall; an inner cannula disposed within outer cannula interior lumen and secured to the outer cannula, the inner cannula having an inner cannula lengthwise axis, an inner cannula circumferential wall extending between an inner cannula proximal end and an inner cannula distal end, the inner cannula circumferential wall defining an inner cannula interior lumen, a pattern of openings extending along a spiral path about the inner cannula lengthwise axis, and a second side port opening extending through the outer cannula circumferential wall and aligned with the first side port opening with respect to the inner cannula lengthwise axis; a side port joint disposed between the outer cannula and the inner cannula and adjacent the second side port opening, the side port joint forming an attachment between the outer cannula and the inner cannula; and a ramp member disposed within the inner cannula interior lumen and defining a ramp surface aligned with second side port opening.

Another example medical device comprises an outer cannula having an outer cannula lengthwise axis and an outer cannula circumferential wall extending between an outer cannula proximal end and an outer cannula distal end, the outer cannula circumferential wall defining an outer cannula interior lumen and a first side port opening extending through the outer cannula circumferential wall, the outer cannula comprising a polymeric material and being free of openings in the outer cannula circumferential wall other than the first side port opening; an inner cannula disposed within outer cannula interior lumen and secured to the outer cannula, the inner cannula having an inner cannula lengthwise axis, an inner cannula circumferential wall extending between an inner cannula proximal end and an inner cannula distal end, the inner cannula circumferential wall defining an inner cannula interior lumen, a pattern of openings extending along a spiral path about the inner cannula lengthwise axis, and a second side port opening extending through the outer cannula circumferential wall and aligned with the first side port opening with respect to the inner cannula lengthwise axis, the inner cannula comprising a metal; a side port joint disposed between the outer cannula and the inner cannula, the side port joint comprising a circumferential joint extending around the second side port opening and forming an attachment between the outer cannula and the inner cannula; and a ramp member disposed within the inner cannula interior lumen and defining a ramp surface aligned with second side port opening.

Methods of making medical devices are described and illustrated herein. An example method of making a medical device comprises passing a first cannula into an interior lumen of a second cannula that defines a pattern of openings extending along a spiral path on its circumferential wall; and securing the first cannula to the second cannula.

Additional understanding of the inventive medical devices and methods can be obtained by reviewing the description of selected examples, below, with reference to the appended drawings.

DETAILED DESCRIPTION OF SELECTED EXAMPLES

The following detailed description and appended drawings describe and illustrate various examples contemplated by the inventors. The description and drawings serve to enable one skilled in the art to make and use the inventive cannulae and medical devices, and to practice the inventive methods; they are not intended to limit the scope of the invention or the protection sought in any manner. The invention is capable of being practiced or carried out in various ways; the examples described herein are merely selected examples of these various ways and are not exhaustive. As such, the language used in the description is to be given the broadest possible scope and meaning.

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular.

As used herein, the term "opening" refers to a passage defined by a member between opposing or substantially opposing surfaces of the member. The term does not require any particular configuration of the passage. Indeed, the term includes rectangular passages, generally rectangular passages, square passages, generally square passages, circular passages, generally circular passages, triangular passages, generally triangular passages, and irregular passages.

As used herein, the term "secured to" refers to the state of one object being attached to another object such that each object is substantially incapable of being axially moved relative to the other object. The term accommodates a small degree of relative axial movement between the objects, such as a slight amount of relative axial movement that might occur as coaxial cannulae that are secured to each other are bent to form a curve. The term does not require a specific type of attachment between the objects, and any suitably type of attachment can be used, including fusion joints, such as joints formed by welding the two objects, and non-fusion joints, such as joints formed by brazing the two objects; mechanical attachments, such as attachments formed by swaging the two objects and attachments formed by crimping the two objects; adhesive attachments, such as attachments formed by inclusion of an adhesive material or member disposed between the two objects; friction-based attachments, such as a friction fit in which the relative sizes of the two objects provide a mechanical securement between the objects; combinations of these types of attachments; and any other suitable type of attachment. Furthermore, the term does not require a specific quality of attachment, and an attachment of any suitable quality can be used, such as a permanent attachment, which requires a degree of destruction of one or both of the objects to remove; a fixed attachment, which requires some manipulation of the attachment to remove; or a temporary attachment, which can be removed simply by manipulating one or both of the objects without imparting a degree of destruction onto either of the objects.

As used herein, the term "slit" refers to an opening that has a rectangular or generally rectangular shape when the surfaces between which the passage extends lie on parallel planes.

Figure 1:
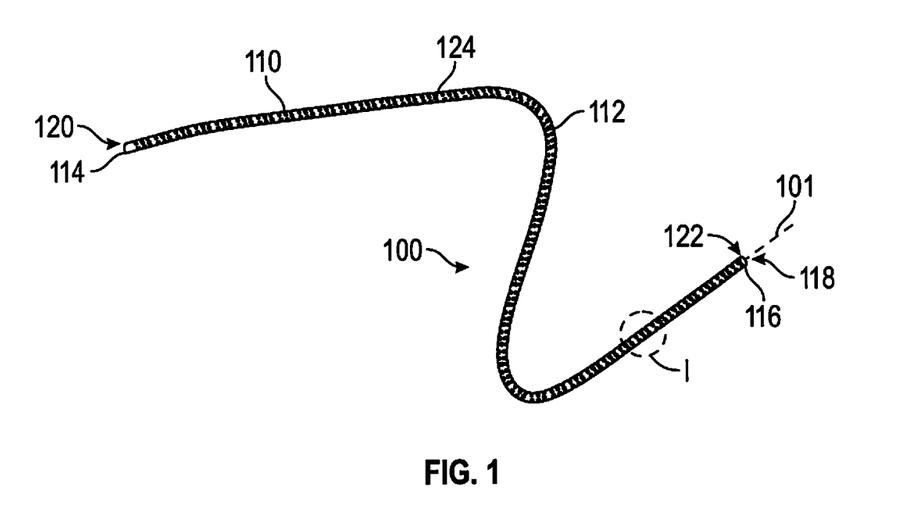
FIG. 1 is a perspective view of a first example medical device.

FIGS. 1, 2, 4A, 4B, and 5 illustrate a first example medical device 100. The medical device 100 includes an inner cannula 150 disposed within and secured to an outer cannula 110 such that the inner 150 and outer 110 cannulae are coaxial. Thus, as best illustrated in FIG. 1, the inner 150 and outer 110 cannulae share common longitudinal axis 101. The outer cannula 110 defines a pattern of openings 124 along a portion of the axial length of the outer cannula 110.

Figure 2:
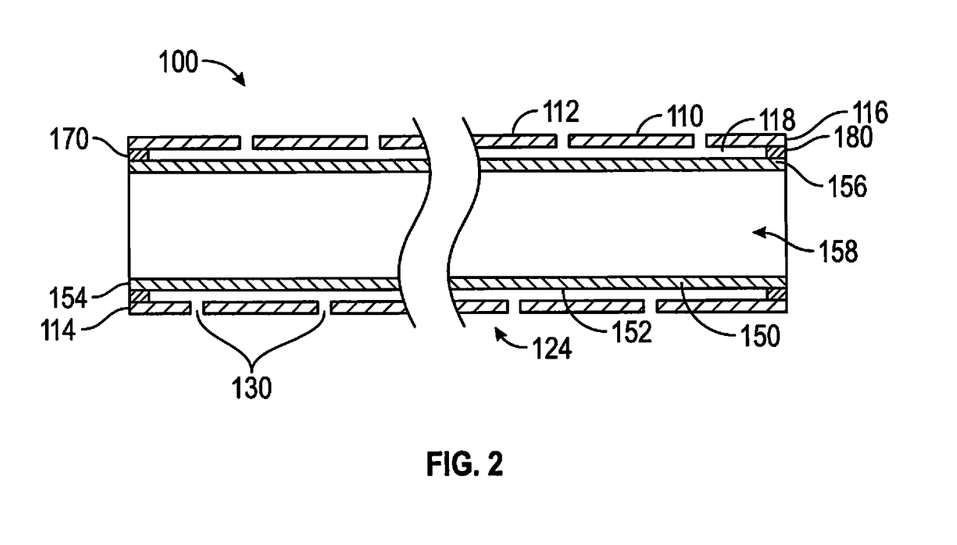
FIG. 2 is a magnified, lengthwise cross-sectional view, partially broken away, of the first example medical device.

Outer cannula 110 is an elongate tubular member having a circumferential wall 112 extending between a proximal end 114 and a distal end 116. The circumferential wall 112 defines an interior lumen 118. A proximal opening 120 on the proximal end 114 provides access to the interior lumen 118. Similarly, a distal opening 122 on the distal end 116 provides access to the interior lumen 118. A longitudinal axis 101 extends centrally through the interior lumen 118.

As best illustrated in FIG. 1, outer cannula 110 defines a pattern of openings 124 that extends along a portion of the axial length of the outer cannula 110. In the illustrated example, the pattern of openings 124 extends along the entire axial length of the outer cannula 110, extending between the proximal 114 and distal 116 ends. The pattern of openings 124 can extend along any suitable portion of the axial length of the outer cannula 110, though, and the entire axial length, as in the illustrated outer cannula 110, is only an example. For a medical device according to a particular example, a skilled artisan will be able to select a suitable portion of the axial length of the outer cannula along which the pattern of openings is to extend based on various considerations, including any need or desire for axial portions having a greater stiffness than that provided by an axial portion along which the pattern of openings extends. For example, if it is desirable to have an axial portion that has the stiffness of the cannula material itself, without any openings, the outer cannula can be made so that the pattern of openings does not extend along the axial portion for which this particular stiffness is desired. It is noted that, while the illustrated embodiment includes an outer cannula 110 that defines a pattern of openings 124 and an inner cannula 150 that is free of openings through the sidewall of the inner cannula 150, an opposite structural arrangement can be used in an embodiment. Thus, a medical device according to an embodiment can include an inner cannula that defines a pattern of openings that extend through its sidewall and an outer cannula that is free of a pattern of openings through its sidewall, other than any desired side port openings that align with any included ramp member and/or side port opening in the inner cannula.

Figure 5:
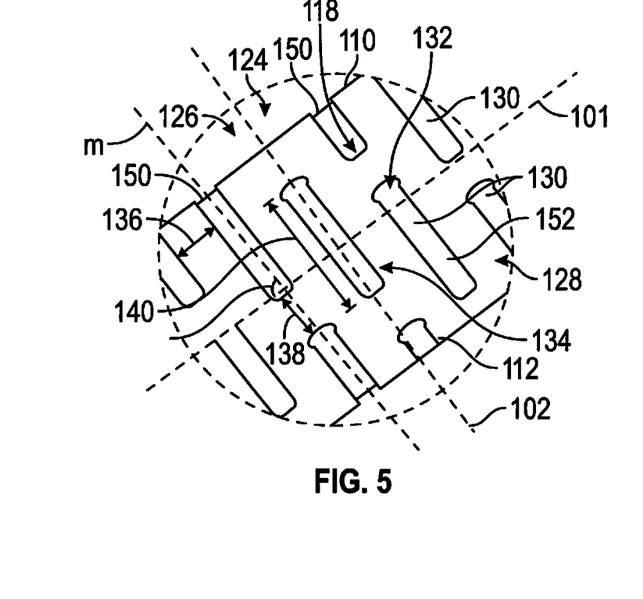
FIG. 5 is a magnified view of area I in FIG. 1.

The pattern of openings can comprise any suitable pattern of openings and a skilled artisan will be able to select a specific pattern of openings for use in a medical device according to a particular embodiment based on various considerations, such as the nature of the material used in the outer and/or inner cannula, the nature of the body vessel within which the medical device is intended to be used, and any desired flexibility for the medical device. The outer cannula 110 of the first example medical device 100 includes an example pattern of openings considered suitable by the inventors. As best illustrated in FIG. 5, this example pattern of openings 124 comprises a plurality of openings 126 arranged in an interrupted spiral 128 that extends circumferentially along the circumferential wall 112 of the outer cannula 110. In the illustrated embodiment, each opening 130 of the plurality of openings 126 comprises a slit that extends through the entire wall thickness of the circumferential wall 112 to provide access to the lumen 118 of the outer cannula 100. Practically, due to the coaxial structure of the medical device 100, each opening 130 provides access to the inner cannula 150, which is disposed within the lumen 118 of the outer cannula 110. Thus, as best illustrated in FIG. 5, each opening of the outer cannula 110 reveals a portion of the circumferential wall 152 of the underlying inner cannula 150.

Also as best illustrated in FIG. 5, the slit of each opening 130 in the example pattern of openings 124 has a generally rectangular shape having a major axis m disposed on a plane that is transverse to the longitudinal axis 101 of the outer cannula 110. In the illustrated embodiment, one end 132 of the slit of each opening 130 has a slightly enlarged width, measured along the minor axis of the oblong rectangle of the slit. This enlarged width can be an artifact of some techniques used for forming the openings 130 in the circumferential wall 112 of the cannula 100, such as laser cutting. Inclusion of the enlarged width, accordingly, is considered optional. The overall pattern of openings 124 takes a spiral 128 configuration relative to the longitudinal axis of the outer cannula 110 because the major axis m of each opening 130 is disposed on a plane that intersects the longitudinal axis 101 of the outer cannula 110 at a non-orthogonal angle α. Thus, opening 134 is slightly skewed relative to transverse axis 102, as are all other openings 130 in the plurality of openings 124.

Inner cannula 150 is an elongate tubular member having a circumferential wall 152 extending between a proximal end 154 and a distal end 156. The circumferential wall 152 defines an interior lumen 158. A proximal opening 160 on the proximal end 154 provides access to the interior lumen 158. Similarly, a distal opening 162 on the distal end 156 provides access to the interior lumen 158. As best illustrated in FIG. 1, in the medical device 100, common longitudinal axis 101 extends centrally through the interior lumen 158 of the inner cannula 150. In example medical device 100, inner cannula 150 does not define any openings in its circumferential wall 152. Indeed, the inner cannula 150 in example medical device 100 defines a continuous circumferential wall that is completely free of any openings that extend through the thickness, partially or completely, of circumferential wall 152.

Both the inner and outer cannula can be made of any suitable material. Furthermore, the inner and outer cannula in a medical device according to a particular embodiment can be made from the same or different materials. A skilled artisan will be able to select an appropriate material for each cannula based on various considerations, including any desired overall stiffness and/or flexibility of the cannula, any desired overall stiffness and/or flexibility of the medical device, and the nature of the body vessel within which the medical device is intended to be used. Metals are considered advantageous for the examples described and illustrated herein, but polymeric, including plastic materials currently considered suitable for use in medical devices, and other materials can be used. Stainless steel is considered particularly advantageous for the example cannulae described and illustrated herein at least because of its well-characterized nature, acceptance as a material used in medical devices temporarily placed within body lumens, and ready availability. Examples of other metals considered suitable for use in cannulae according to particular examples include cobalt-chrome and superelastic alloys, such as nickel-titanium alloys. Examples of polymeric materials considered suitable for use in cannulae according to particular examples include polyamide materials, such as nylon, heat shrink materials, such as polyethylene terephthalate (PET), and other polymeric materials. A cannula can include multiple materials, too, if desired. For example, an axial length of one material can be joined to an axial length of another material to create a cannula. The pattern of openings in such a cannula can be disposed on any suitable axial portion of the cannula, such as an axial portion comprising only the first material, an axial portion comprising only the second material, or an axial portion comprising both the first and the second material.

The inventors have determined that use of different materials for the inner and outer cannulae provides desirable performance characteristics, including desirable flexibility, for the medical devices. For example, the inventors have determined that including an outer cannula formed from stainless steel and an inner cannula formed from nitinol or another superelastic material provides a medical device having desirable performance characteristics. Furthermore, including an outer cannula formed from a polymeric material and an inner cannula formed from a metal provides a medical device having desirable performance characteristics. Indeed, a medical device having an inner cannula formed from a metal and that defines a pattern of openings that extend through its sidewall and an outer cannula formed from a polymeric material and that is free of openings through its sidewall provides a medical device with desirable performance characteristics. In these embodiments, inclusion of an inner cannula formed from stainless steel, cobalt-chrome, or a superelastic alloy, such as a nickel-titanium alloy, with an outer cannula formed from a heat shrink material, such as PET, is considered particularly advantageous.

It is noted that a medical device according to a particular example can include inner and outer cannulae that each define a lumen of any suitable diameter and that the dimensions of the lumen of the cannulae described and illustrated herein are illustrative only. A skilled artisan will be able to select an appropriate lumen size for each cannula in a medical device according to a particular example based on various considerations, including the dimensions of the lumen of the body vessel within which the medical device is intended to be used. The inventors have determined that use of an inner cannula that defines a lumen having an inner diameter suitable to allow one or more standard sized medical wires to be passed through the lumen is desirable. For example, an inner cannula that defines an interior lumen sized to allow a 0.018" wire to be passed through its lumen is considered suitable and, indeed, advantageous. The lumen of an outer cannula in a medical device according to an embodiment should be sized to allow the inner cannula to be disposed within the lumen and secured to the outer cannula as described herein. Furthermore, it is considered advantageous for the outer cannula to have an outer diameter that allows the medical device to be used in conjunction with components of catheters and other medical devices. For example, an outer cannula that defines an outer diameter of about 0.035" is considered suitable and, indeed, advantageous at least because this size allows the medical device to be used as an inner member in conjunction with another medical device, such as a wireguide over which a catheter, delivery system, or other medical device can be navigated.

It is noted that a medical device according to a particular example can include inner and outer cannulae that each have a circumferential wall of any suitable wall thickness and that the wall thicknesses of the circumferential walls of the cannulae described and illustrated herein are illustrative only. Furthermore, the inner and outer cannula in a medical device according to a particular embodiment can have circumferential walls that have the same or different wall thicknesses. A skilled artisan will be able to select an appropriate wall thickness for each cannula in a medical device according to a particular embodiment based on various considerations, including any desired overall stiffness of the individual cannula and/or the medical device.

As best illustrated in FIG. 2, inner cannula 150 is disposed within lumen 118 of outer cannula 110 and is secured to outer cannula 110 with proximal joint 170 and distal joint 180. Any suitable joint can be used in a medical device according to a particular embodiment to secure the inner cannula 150 to the outer cannula 110, and a skilled artisan will be able to select appropriate joints based on various considerations, including the nature of the materials of the inner and outer cannula, any desired access to the interior lumen of the outer cannula, and other considerations. In the illustrated example, each of the proximal 170 and distal 180 joints comprises a circumferential weld joint formed between the inner 150 and outer 110 cannulae. Other examples of suitable joints included spot weld joints (i.e., non-circumferential weld joints), brazing joints, and solder joints.

As alternatives to joints in medical devices according to other embodiments, the inner cannula can be secured to the outer cannula through other types of attachments, such as mechanical attachments (e.g., swaging and/or crimping the cannulae together), and the inclusion of one or more separate joining members disposed between and directly attached to each of the inner and outer cannula to form an attachment, such as the inclusion of an adhesive composition or member between the cannulae. It is noted, too, that different types of attachments can be used to join cannulae in a medical device according to a particular embodiment. For example, it may be desirable to include a circumferential weld joint at one end of a medical device and a series of non-circumferential spot weld joints at another end of the medical device. As another example, it may be desirable to include a circumferential weld joint at one end of a medical device and a mechanical attachment at the other end of the medical device.

Figure 4A:
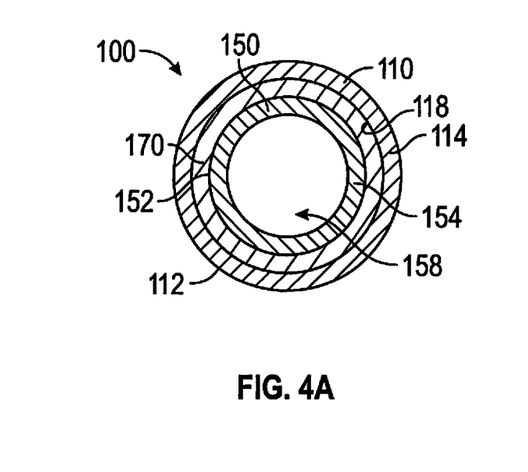
FIG. 4A is a proximal end view of the first example medical device.
Figure 4B:
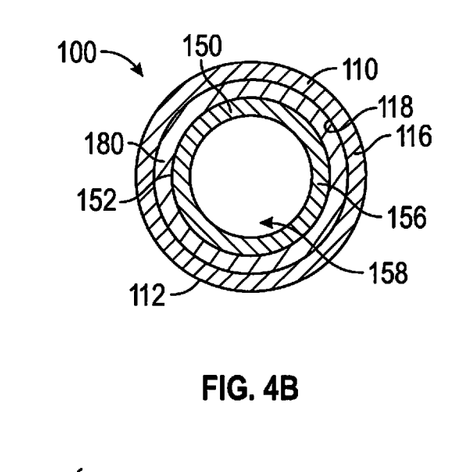
FIG. 4B is a distal end view of the first example medical device.

No matter the type or types of attachment used in a medical device according to a particular embodiment, each attachment can be positioned at any suitable location along the axial length of the medical device. For a medical device according to a particular embodiment, a skilled artisan will be able to determine a suitable location for each attachment based on various considerations, including any desired access to the interior lumen of the outer cannula and other considerations. As best illustrated in FIGS. 2 and 4A, the proximal joint 170 in medical device 100 is located flush with the proximal end 114 of the outer cannula 110 and the proximal end 154 of the inner cannula 150. Similarly, as best illustrated in FIGS. 2 and 4B, the distal joint 180 is located flush with the distal end 116 of the outer cannula 110 and the distal end 156 of the inner cannula 150. This arrangement of the attachments is considered advantageous for medical devices according to embodiments for which no access to the lumen of the outer cannula through the proximal and distal openings of the outer cannula is desired.

Figure 3A:
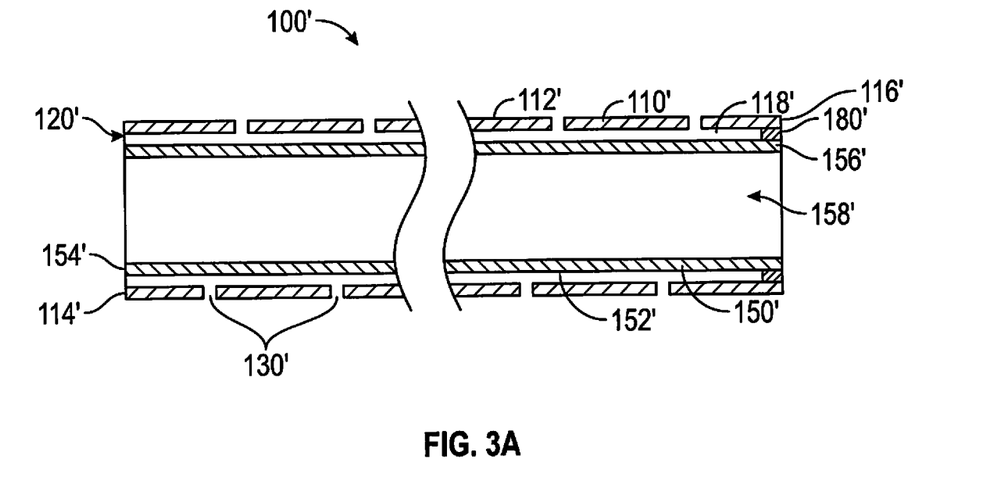
FIG. 3A is a magnified, lengthwise cross-sectional view, partially broken away, of an alternative medical device.

FIG. 3A illustrates a first alternative medical device 100' that includes only a single attachment. The medical device 100' is identical to the first example medical device 100, except as described below. Thus, medical device 100' includes an inner cannula 150' disposed within and secured to an outer cannula 110' such that the inner 150' and outer 110' cannulae are coaxial. The outer cannula 110' defines a pattern of openings 124' along a portion of the axial length of the outer cannula 110'. Outer cannula 110' is an elongate tubular member having a circumferential wall 112' extending between a proximal end 114' and a distal end 116'. The circumferential wall 112' defines an interior lumen 118'. Inner cannula 150' is an elongate tubular member having a circumferential wall 152' extending between a proximal end 154' and a distal end 156'. The circumferential wall 152' defines an interior lumen 158'.

In this embodiment, only a single attachment secures the inner cannula 150' to the outer cannula 110'. Distal joint 180' is a circumferential weld joint formed between the inner 150' and outer 110' cannulae and disposed within the interior lumen 118' of the outer cannula 110'. The proximal end of the medical device 100' is free of attachments between the inner 150' and outer 110' cannulae. As a result, proximal opening 120' is not blocked and provides fluid access to the interior lumen 118' of the outer cannula 110' from the environment external to the medical device 100'. This structural arrangement is considered advantageous at least because it simplifies manufacturing of medical devices while still providing the desired securement between the inner 150' and outer 110' cannula. Furthermore, this structural arrangement allows for a slight amount of relative axial movement between the cannulae 150', 110' that might occur as the medical device 100' is bent to form a curve.

Figure 3B:
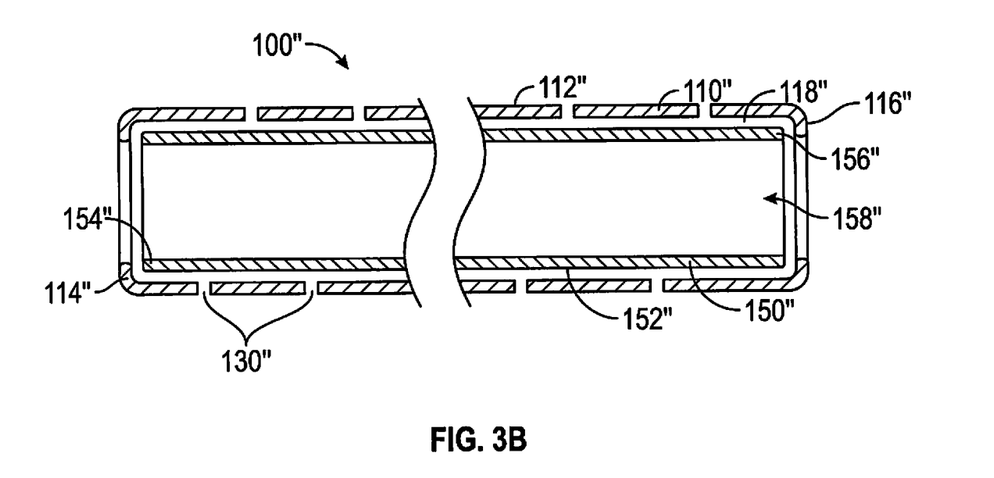
FIG. 3B is a magnified, lengthwise cross-sectional view, partially broken away, of an alternative medical device.

FIG. 3B illustrates a second alternative medical device 100" that includes two mechanical attachments. The medical device 100" is identical to the first example medical device 100, except as described below. Thus, medical device 100" includes an inner cannula 150" disposed within and secured to an outer cannula 110" such that the inner 150" and outer 110" cannulae are coaxial. The outer cannula 110" defines a pattern of openings 124" along a portion of the axial length of the outer cannula 110". Outer cannula 110" is an elongate tubular member having a circumferential wall 112" extending between a proximal end 114" and a distal end 116". The circumferential wall 112" defines an interior lumen 118". Inner cannula 150" is an elongate tubular member having a circumferential wall 152" extending between a proximal end 154" and a distal end 156". The circumferential wall 152" defines an interior lumen 158".

In this embodiment, each of the proximal 114" and distal 116" ends of the outer cannula 110" extends inwardly into the interior lumen 118' of the outer cannula 110' such that the inner cannula 150" is held captive in the interior lumen 118" of the outer cannula 110". As a result of this captivating structure, the inner cannula 150" is secured to the outer cannula 110". Also, neither the proximal opening 120" or the distal opening 122" of the outer cannula 110" is completely blocked, providing a degree of fluid access to the interior lumen 118" of the outer cannula 110" from the environment external to the medical device 100". It is noted, though, that the proximal and distal ends of an outer cannula in a medical device according to an embodiment could be structured to completely block fluid access to the interior lumen of the outer cannula, if desired. A seal and/or sealing member can be included if desired. The structural arrangement of the embodiment illustrated in FIG. 3B is considered advantageous at least because it simplifies manufacturing of medical devices while still providing the desired securement between the inner 150" and outer 110" cannula. Furthermore, this structural arrangement also allows for a slight amount of relative axial movement between the cannulae 150", 110" that might occur as the medical device 100" is bent to form a curve.

While the outer cannula 110" of the medical device 100" illustrated in FIG. 3B is illustrated as having ends 114", 116" that extend inwardly into the interior lumen 118" of the outer cannula 110", it is noted that an additional element or composition can be attached to the interior surface 180" of the circumferential wall 112" of the outer cannula 110" to achieve the desired structural arrangement between the inner 150" and outer 110" cannulae. For example, a partial or full circumferential ring member could be secured to the interior surface 180" of the circumferential wall 112" of the outer cannula 110" at the proximal 114" and distal 116" ends of the outer cannula 110", or at other suitable locations.

Figure 6:
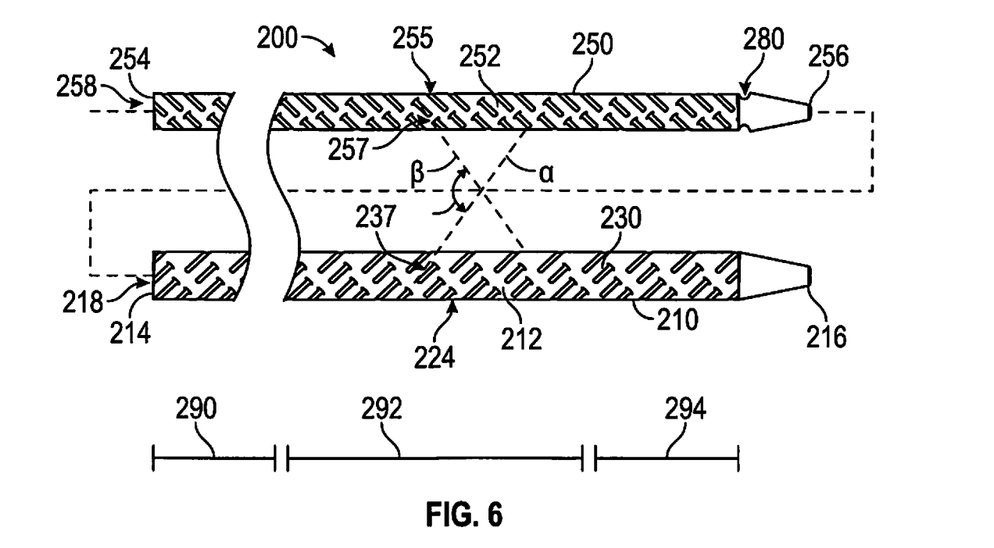
FIG. 6 is an exploded view of a second example medical device.
Figure 7:
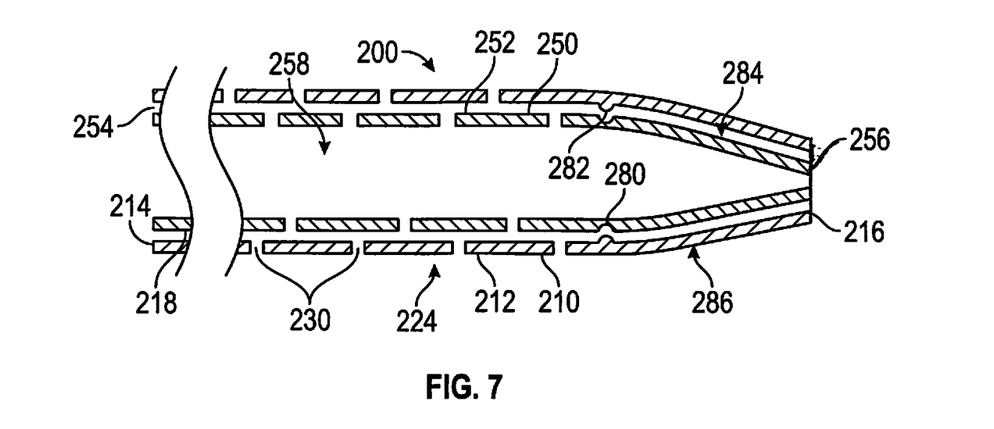
FIG. 7 is a magnified, lengthwise cross-sectional view, partially broken away, of the second example medical device.

FIGS. 6 and 7 illustrate a second example medical device 200. The medical device 200 includes an inner cannula 250 disposed within and secured to an outer cannula 210 such that the inner 250 and outer 210 cannulae are coaxial. The outer cannula 210 defines a pattern of openings 224 along a portion of the axial length of the outer cannula 210. Outer cannula 210 is an elongate tubular member having a circumferential wall 212 extending between a proximal end 214 and a distal end 216. The circumferential wall 212 defines an interior lumen 218. Inner cannula 250 is an elongate tubular member having a circumferential wall 252 extending between a proximal end 254 and a distal end 256. The circumferential wall 252 defines an interior lumen 258.

In this embodiment, the inner cannula 250 is secured to the outer cannula 210 by a mechanical attachment formed between the cannulae 250, 210. Specifically, in this embodiment, the circumferential wall 252 defines a circumferential groove 280 on its outer surface and the circumferential wall 212 of the outer cannula defines a circumferential projection 282 that extends inwardly into the interior lumen 218 of the outer cannula. As best illustrated in FIG. 7, the inner cannula 250 is secured to the outer cannula when the circumferential projection 282 of the outer cannula 210 is disposed within the circumferential groove 280 of the inner cannula 250.

Also in this embodiment, the inner cannula 250 defines a taper 284 at its distal end 256. Similarly, the outer cannula 210 defines a complimentary taper 286 at its distal end 216. Inclusion of complimentary tapers 284, 286 is considered advantageous at least because the structural arrangement provides a transition from a smaller outer diameter to a larger outer diameter, which can increase the usability of the medical device 200, and also because inclusion of complimentary tapers contributes to the securement of the inner cannula 250 to the outer cannula. As best illustrated in FIG. 7, it is considered advantageous to position the circumferential groove 280 at an axial location on the inner cannula 250 where the portion of the inner cannula 250 having the maximum outer diameter transitions into the taper 284. Similarly, it is considered advantageous to position the circumferential projection 2820 at an axial location on the outer cannula 210 where the portion of the outer cannula 210 having the maximum outer diameter transitions into the taper 286. It is noted that, while medical device 200 is illustrated without another attachment between the inner 250 and outer 210 cannulae, additional attachments can be included if desired. For example, a weld joint could be included between the proximal end 254 of the inner cannula 250 and the proximal end 214 of the outer cannula 210.

In this embodiment, pattern of openings 224 extends along a portion of the axial length of the outer cannula 210 that is less than the entire axial length of the outer cannula. As a result, a portion 290 of the axial length of the outer cannula 210 is free of openings in the circumferential wall 212 of the outer cannula 210 while other portions 292, 294 of the axial length of the outer cannula 210 includes openings 230 in the circumferential wall 212. Also, while both portions 292, 294 include openings 230 in the circumferential wall 212, the pattern of openings 224 is different in these two portions. The pattern of openings 224 extends along portion 292 of the axial length of the outer cannula 210 along a spiral having a continuous pitch. That is, the turns of the spiral formed by the openings 230 in portion 292 are separated by the same or substantially the same distance through portion 292 of the axial length of outer cannula 210. In portion 294, however, the pattern of openings 224 extends along the portion 294 of the axial length of outer cannula 210 along a spiral having a progressive pitch. That is, the turns of the spiral formed by the openings 230 in portion 292 are separated by different distances throughout portion 294 of the axial length of outer cannula 210. In the illustrated embodiment, the pitch increases along portion 294 of the axial length of outer cannula 210 as the spiral formed by the openings 230 extends toward distal end 216 of outer cannula 210. This structural arrangement is considered advantageous at least because it provides greater flexibility to the outer cannula at the distal end 216, which lies in portion 294 of the axial length of the outer cannula 210, and relative rigidity at the proximal end 214, which lies in portion 290 of the axial length of the outer cannula 210. Central portion 294 of the axial length of the outer cannula 210 provides a balanced and consistent amount of flexibility along its length. It is noted that, in a medical device according to a particular embodiment, an outer cannula can include a portion having no openings in the circumferential wall, a portion having openings arranged in a spiral having a continuous pitch, and/or a portion having openings arranged in a spiral having a progressive pitch arranged in any suitable combination along its axial length.

Also in this embodiment, the inner cannula 250 defines a pattern of openings 255 along a portion of the axial length of the inner cannula 210. Thus, in this embodiment, the circumferential wall 252 of the inner cannula 250 defines a pattern of openings 255 and the circumferential wall 212 of the outer member 210 defines a pattern of openings 224. It is considered advantageous that the pattern of openings 255 on the inner cannula 250 extend along a spiral path that has an opposite clock orientation to the spiral path along which the pattern of openings 224 extends on the outer cannula 210. That is, as the spiral path along which the pattern of openings 255 on the inner cannula 250 winds around the lengthwise axis 201 of the medical device 200, it proceeds toward the distal end 256 of the inner cannula 250 in a counter-clockwise manner. In contrast, as the spiral path along which the pattern of openings 224 on the outer cannula 210 winds around the lengthwise axis 201 of the medical device 200, it proceeds toward the distal end 216 of the outer cannula 210 in a clockwise manner Furthermore, as best illustrated in FIG. 6, the pattern of openings 255 on the inner cannula 250 in this embodiment extends along a spiral path such that a lengthwise axis β of one opening 257 of the pattern of openings 255 of the inner cannula 250 intersects a lengthwise axis α of one opening 237 of the pattern of openings 224 of the outer cannula 210. The axes β, a can intersect at any suitable angle γ. The inventors have determined, however, that an angle γ of between about 15° and about 135° is considered suitable. An angle γ between about 45° and about 115° is also considered suitable. An angle γ between about 60° and about 105° is also considered suitable. An angle γ between about 75° and about 95° is also considered suitable. An angle γ of about 90° is also considered suitable. Inclusion of a pattern of openings 255 on the inner cannula 250 is considered advantageous at least because it provides an additional degree of flexibility to the medical device 200. Inclusion of a pattern of openings 255 on the inner cannula 250 that extends along a spiral that is counter rotating with respect to the spiral along which the pattern of openings 224 extends along the outer cannula 210, as described above, is considered advantageous at least because this structural arrangement ensures that openings in the respective patterns of openings 255, 224 may cross one another but will never align with one another, which could present an opportunity for binding and/or kinking.

Figure 8:
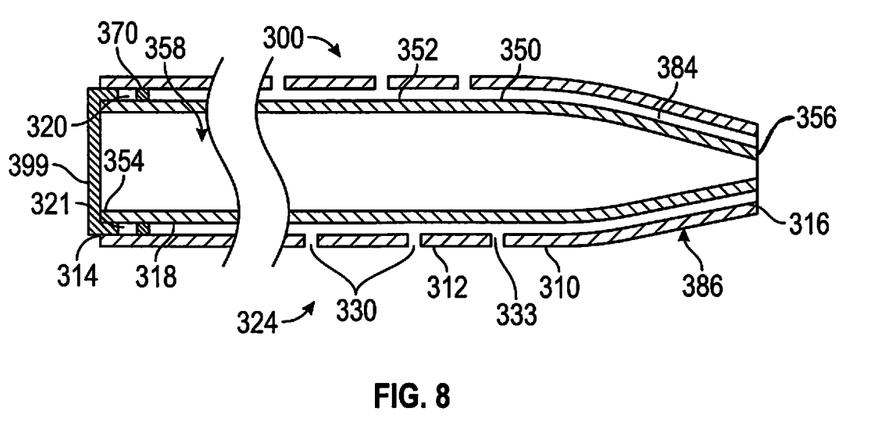
FIG. 8 is a magnified, lengthwise cross-sectional view, partially broken away, of a third example medical device.

FIG. 8 illustrates a third example medical device 300. The medical device 300 includes an inner cannula 350 disposed within and secured to an outer cannula 310 such that the inner 350 and outer 310 cannulae are coaxial. The outer cannula 310 defines a pattern of openings 324 along a portion of the axial length of the outer cannula 310.

In this embodiment, the inner cannula 350 is secured to the outer cannula 310 by proximal joint 370 disposed between the cannulae 350, 310. Also in this embodiment, the inner cannula 350 defines a taper 384 at its distal end 356. Similarly, the outer cannula 310 defines a complimentary taper 386 at its distal end 316.

In this embodiment, the proximal joint 370 is axially spaced from the proximal ends 314, 354 of the outer 310 and inner 350 cannulae. This structural arrangement leaves the proximal opening 320 accessible. In the illustrated embodiment, the proximal joint 370 is a partial circumferential weld joint, which forms a circumferential channel 321 between the proximal end 354 of the inner cannula 350 and the proximal end 314 of the outer cannula 310. A proximal cap 399 is disposed into the circumferential channel 321. The cap 399 blocks access to the interior lumen 318 of the outer cannula 310 and to the interior lumen 358 of the inner cannula 350. Furthermore, the proximal cap 399 can function to prevent blood or other fluid from entering one or both of the interior lumens 318, 358 on the distal end of the medical device and travelling through the interior lumens 318, 358 through capillary action.

Also in this embodiment, a coating 333 is disposed on the outer cannula 310. Any suitable coating can be used in a medical device according to a particular embodiment, and a skilled artisan will be able to select a suitable coating for a specific medical device based on various considerations, including any desired flexibility, hydrophilicity, and/or lubricity. If included, any conventional hydrophilic, lubricious, and/or heat-shrink polymeric coating considered suitable for use in medical devices is considered suitable and acceptable.

Figure 9:
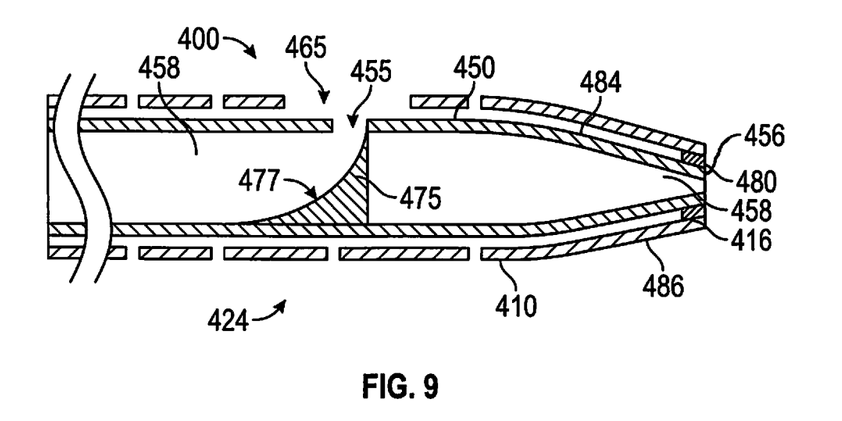
FIG. 9 is a lengthwise cross-sectional view, partially broken away, of a fourth example medical device.

FIG. 9 illustrates a fourth example medical device 400. The medical device 400 includes an inner cannula 450 disposed within and secured to an outer cannula 410 such that the inner 450 and outer 410 cannulae are coaxial. The outer cannula 410 defines a pattern of openings 424 along a portion of the axial length of the outer cannula 410. The inner cannula 450 defines a taper 484 at its distal end 456. Similarly, the outer cannula 410 defines a complimentary taper 486 at its distal end 416.

In this embodiment, the inner cannula 450 is secured to the outer cannula 410 by distal joint 480 disposed between the cannulae 450, 410. Also in this embodiment, the inner cannula 410 defines a first side port opening 455 and the outer cannula 410 defines a second side port opening 465. Also, a ramp member 475 is disposed within the interior lumen 458 of the inner cannula 450 and defines a ramp surface 477 that leads to the first side port opening 455.

The first side port opening 455 provides access to the interior lumen 458 of the inner cannula 450 and is aligned with the ramp surface 477. As such, the first side port opening 455 provides a passageway for a member, such as a wireguide or other elongate member, to exit the interior lumen 458 of the inner cannula 450 following distal advancement within the interior lumen 458 of the inner cannula 450. The second side port opening 465 is aligned with the first side port opening 455 such that it continues the passageway provided by the first side port opening 455 and, ultimately, allows a member exiting the interior lumen 458 of the inner cannula 450 to enter the environment external to the medical device 450.

Each of the first 455 and second 465 side port openings can have any suitable size, shape and configuration, and a skilled artisan will be able to select appropriate size, shape and configuration parameters for side port openings in a medical device according to a particular embodiment based on various considerations, including any size, shape and configuration parameters of an inner member intended to be advanced the interior lumen of the inner cannula of the medical device, the axial distance of the side port openings from the distal end of the medical device, and other considerations. Examples of suitable side port openings include circular side port openings, such as the first 455 and second 465 side port openings in the illustrated embodiment, elongate circular openings, ovoid openings, and combinations of different openings, such as an ovoid opening on one cannula and a circular opening on the other cannula in a medical device according to an embodiment. In the illustrated embodiment, each of the first 455 and second 465 side port openings is a circular opening through the circumferential wall of the respective cannula 410, 450. Also, the second side port opening 465 is larger in diameter than the first side port opening 455. This relative sizing is considered advantageous at least because it allows some relative axial movement, i.e., translation, to occur between the outer cannula 410 and the inner cannula 450, such as occurs when the medical device 400 is curved or bent slightly, without creating an impediment in the passageway between the external environment to the internal lumen 458 of the inner cannula 450. Any suitable difference in the relative sizes of the first and second side port openings can be used in a medical device according to a particular embodiment. Generally, it is considered advantageous to use a larger difference in the relative sizes of the first and second side port openings as the axial distance between the center of the openings and an attachment between the cannulae in the medical device increases. At greater distances from an attachment between the cannula, a greater amount of relative axial movement between the cannulae can occur, which requires a larger difference in the relative sizes of the first and second side port openings to ensure that the passageway provided by the openings is not impeded when the medical device is curved or bent slightly. It is noted, though, that any suitable first and second side port openings, including first and second side port openings of the same size, and a first side port opening that is smaller than a second side port opening. Also, it is noted that an attachment between the cannula at or near a pair of side port openings in the inner and outer cannulae can be included in a medical device according to an embodiment, such as a spot weld between the inner and outer cannulae, a circumferential weld that surrounds the side port opening in the inner cannula, and any other suitable attachment. Inclusion of an attachment at or near the side port openings in a medical device according to an embodiment can be advantageous if it is desirable to prevent localized translation between the inner and outer cannulae at the location of the side port openings.

The ramp member 475 provides a ramp surface 477 that guides a member being axially advanced in a distal direction within the interior lumen 458 of the inner cannula 450 toward the first side port opening 455. As such, the ramp surface 477 is generally aligned with the first side port opening 455. Indeed, in the illustrated embodiment, the ramp surface 477 is continuous with the first side port opening 455. A ramp member can have any suitable size, shape and configuration, and a skilled artisan will be able to select suitable size, shape and configuration parameters for a ramp member in a medical device according to a particular embodiment based on various considerations, including the materials from which the cannulae of the subject medical device are formed, the nature and flexibility of any elongate member intended to be advanced within the interior lumen of the inner cannula and through the side port openings of the subject medical device, and other considerations. In the illustrated embodiment, the ramp member 475 is a separate member that is disposed within the interior lumen 458 of the inner cannula 450 and secured to the inner cannula 450, such as with an adhesive or mechanical attachment. It is noted, though, that a ramp member integrally formed with an inner cannula could also be used. Also in the illustrated embodiment, the ramp surface 477 is a parabolic surface. The inclusion of a parabolic ramp surface 477, or a ramp surface defining another suitable curve, is considered advantageous for use with medical devices within which a relatively flexible inner member, such as a wireguide, may be used as such ramp surfaces can effectively guide such inner members toward and through the side port openings 455, 457. For medical devices within which a relatively stiff inner member, such as a cannula or other member, may be used, a substantially flat, planar, or non-curved ramp surface is considered advantageous at least because such ramp surfaces can effectively guide such inner members toward and through the side port openings 455, 457.

In this embodiment, the distal joint 480 is flush with the distal ends 416, 456 of the outer 410 and inner 450 cannulae. In the illustrated embodiment, the distal joint 480 is a complete circumferential weld joint, which forms a circumferential seal between the distal end 456 of the inner cannula 450 and the distal end 416 of the outer cannula 410.

Figure 9A:
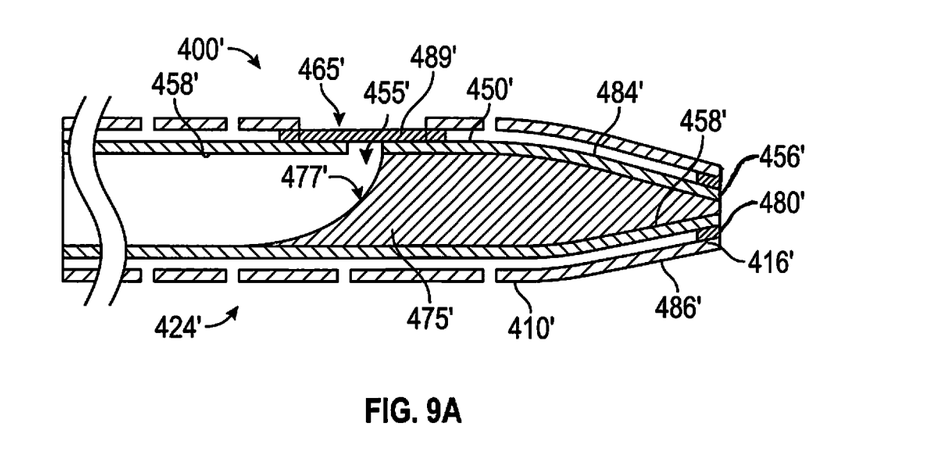
FIG. 9A is a lengthwise cross-sectional view, partially broken away, of an alternative medical device.

FIG. 9A illustrates an alternative medical device 400'. The medical device 400' is identical to the fourth example medical device 400 described above, except as described below. Thus, medical device 400' includes an inner cannula 450' disposed within and secured to an outer cannula 410' such that the inner 450' and outer 410' cannulae are coaxial. The outer cannula 410' defines a pattern of openings 424' along a portion of the axial length of the outer cannula 410'. The inner cannula 450' defines a taper 484' at its distal end 456'. Similarly, the outer cannula 410' defines a complimentary taper 486' at its distal end 416'. The inner cannula 450' is secured to the outer cannula 410' by distal joint 480' disposed between the cannulae 450', 410'. The inner cannula 410' defines a first side port opening 455' and the outer cannula 410' defines a second side port opening 465'. A ramp member 475' is disposed within the interior lumen 458' of the inner cannula 450' and defines a ramp surface 477' that leads to the first side port opening 455'. The first side port opening 455' provides access to the interior lumen 458' of the inner cannula 450' and is aligned with the ramp surface 477'. The second side port opening 465' is aligned with the first side port opening 455' such that it continues the passageway provided by the first side port opening 455' and, ultimately, allows a member exiting the interior lumen 458' of the inner cannula 450' to enter the environment external to the medical device 400'.

In this embodiment, the ramp member 475' extends distally beyond the first side port opening 455' toward and to the distal end 456' of the inner cannula 450'. Inclusion of a ramp member that extends axially beyond the side port opening in a medical device according to an embodiment is considered advantageous at least because it provides additional surface area for securement of the ramp member within the inner cannula as compared to the ramp member 475 in the medical device 400 described above.

Also in this embodiment, a side port joint 489' is disposed around the side port opening 455' in the inner cannula and between the outer cannula 410' and the inner cannula 450'. In the illustrated embodiment, the side port joint 489' is a complete circumferential weld joint, which forms a circumferential seal between the inner cannula 450' and the outer cannula 410' around the first side port opening 455' and beneath the edge of the outer cannula 410' that forms the second side port opening 465'. While the circumferential weld joint is considered advantageous at least because it limits translation between the cannulae 410', 450' at the location of the side port opening 455', 465', other suitable attachments can be used, including those described above, such as spot welds, adhesives, crimps, and other attachments.

Figure 9B:
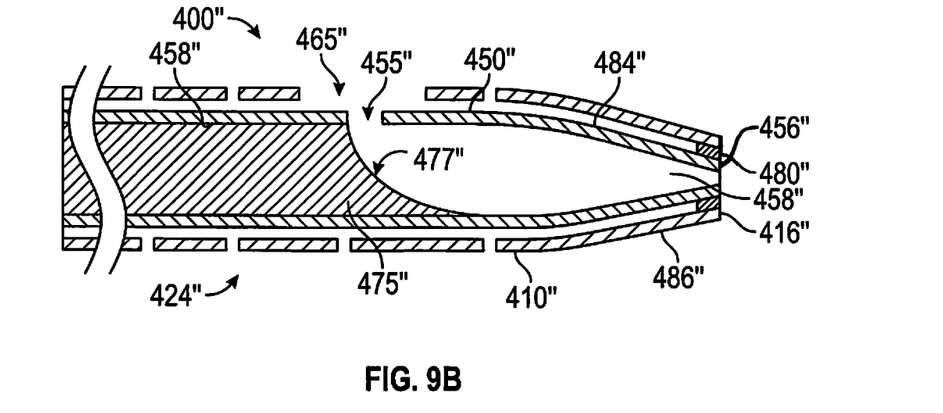
FIG. 9B is a lengthwise cross-sectional view, partially broken away, of an alternative medical device.

FIG. 9B illustrates another alternative medical device 400". The medical device 400" is identical to the fourth example medical device 400 described above, except as described below. Thus, medical device 400" includes an inner cannula 450" disposed within and secured to an outer cannula 410" such that the inner 450" and outer 410" cannulae are coaxial. The outer cannula 410" defines a pattern of openings 424" along a portion of the axial length of the outer cannula 410". The inner cannula 450" defines a taper 484" at its distal end 456". Similarly, the outer cannula 410" defines a complimentary taper 486" at its distal end 416". The inner cannula 450" is secured to the outer cannula 410" by distal joint 480" disposed between the cannulae 450", 410". The inner cannula 410" defines a first side port opening 455" and the outer cannula 410" defines a second side port opening 465". A ramp member 475" is disposed within the interior lumen 458" of the inner cannula 450" and defines a ramp surface 477" that leads to the first side port opening 455". The first side port opening 455" provides access to the interior lumen 458" of the inner cannula 450" and is aligned with the ramp surface 477". The second side port opening 465" is aligned with the first side port opening 455" such that it continues the passageway provided by the first side port opening 455" and, ultimately, allows a member exiting the interior lumen 458" of the inner cannula 450" to enter the environment external to the medical device 400".

In this embodiment, the ramp member 475" is positioned in the opposite axial orientation, such that the ramp surface 477" faces the distal end 456" of the inner cannula 450" and the body of the ramp member 475" extends proximally from the first side port opening 455" toward and to the proximal end of the inner cannula 450" and the medical device 400". Inclusion of a ramp member having this structural configuration provides a relatively short interior lumen 458" of the inner cannula 450" and provides access through the distal end 456" of the inner cannula 450". This configuration is considered advantageous for use in medical devices according to embodiments that are intended for use in or with rapid exchange medical devices, kits, and methods.

Figure 10:
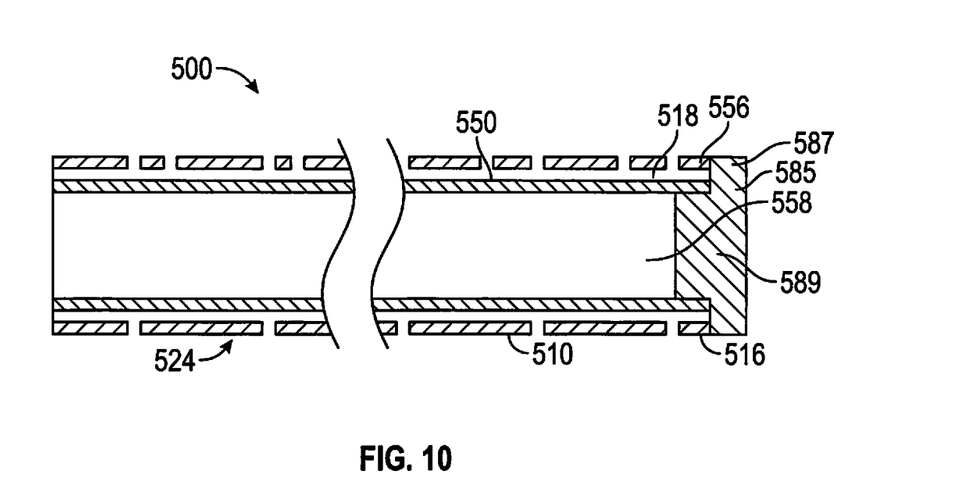
FIG. 10 is a lengthwise cross-sectional view, partially broken away, of a fifth example medical device.

FIG. 10 illustrates a fifth example medical device 500. The medical device 500 includes an inner cannula 550 disposed within and secured to an outer cannula 510 such that the inner 550 and outer 510 cannulae are coaxial. The outer cannula 510 defines a pattern of openings 424 along a portion of the axial length of the outer cannula 510.

In this embodiment, a plug member 585 is disposed in the distal opening of the interior lumen 558 of the inner cannula 550. The inner cannula 550 is secured to the outer cannula 510 by mutual attachment of the respective distal ends 516, 556 of the outer 510 and inner 550 cannulae, respectively, to the plug member 585.

The plug member can have any suitable size, shape and configuration, and a skilled artisan will be able to determine appropriate size, shape and configuration parameters for a plug in a medical device according to a particular embodiment based on various considerations, including the dimensions and configurations of the inner and outer cannulae of the subject medical device. In the illustrated embodiment, the plug member 585 has a distal flange portion 587 that is attached to the outer cannula 510 and an inner base portion 589 that is attached to the inner cannula 550 and that extends into the interior lumen 558 of the inner cannula 550. The plug member 585 is attached to the outer 510 and inner cannulae 510 in a manner that maintains a clearance between the outer 510 and inner 550 cannulae that comprises a portion of the interior lumen 518 of the outer cannula 510.

The plug member can be formed of any suitable material and a skilled artisan will be able to select an appropriate material for a plug in a medical device according to a particular embodiment based on various considerations, including the materials of the cannulae of the subject medical device and the nature of the body vessel within which the medical device is intended to be use. Examples of materials considered suitable for a plug member include, but are not limited to, elastomeric materials, such as rubber materials, polymeric materials, and metals. Furthermore, the plug member can be attached to the inner and outer cannulae in any suitable manner, and a skilled artisan will be able to select an appropriate attachment in a medical device according to a particular embodiment based on various considerations, including the materials used in the plug and inner and outer cannulae of the subject medical device. Examples of suitable attachments include, but are not limited to, adhesive attachments and mechanical attachments.

Figure 11:
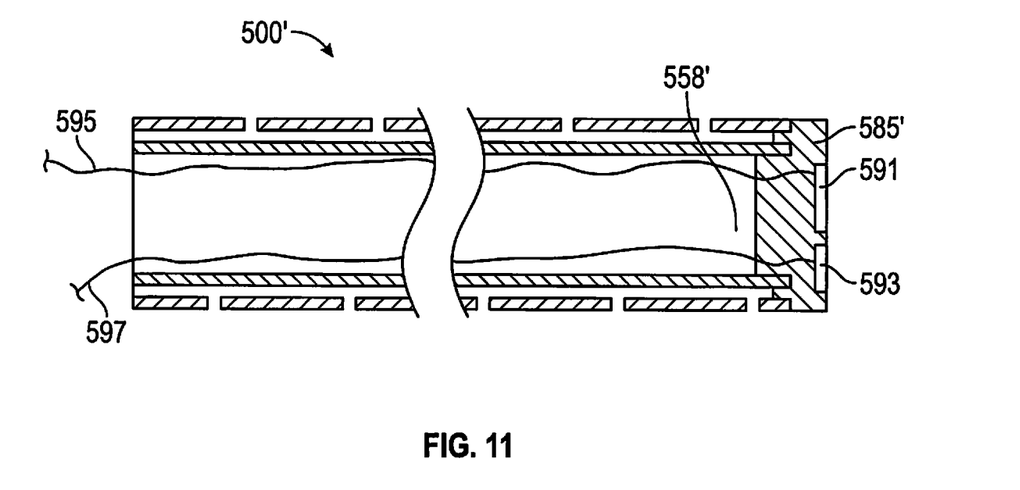
FIG. 11 is a lengthwise cross-sectional view, partially broken away, of an alternative medical device.

If included, a plug member can provide additional functionality to a medical device. For example, FIG. 11 illustrates an alternative medical device 500' that includes a plug member 585' that includes first 591 and second 593 sensors embedded within the plug member 585'. In the illustrated embodiment, a first wire 595 is in electrical communication with the first sensor 591 and extends through the interior lumen 558' of the inner cannula 550'. Similarly, a second wire 597 is in electrical communication with the second sensor 593 and extends through the interior lumen 558' of the inner cannula 550'. It is noted that any wires operably connected to the sensors in a medical device according to an embodiment could, alternatively, extend through the interior lumen of the outer cannula. In these embodiments, the wires are maintained in the clearance between the outer and inner cannulae. If included, any suitable sensor can be used and a skilled artisan will be able to select one or more appropriate sensors based on various considerations, including the nature of the body vessel within which a particular medical device is intended to be used, and the nature of any body fluids within a particular body vessel within which the medical device is intended to be used. Examples of suitable sensors include flow sensors, pressure sensors, temperature sensors, chemical detectors, and other sensors. Also, it is noted that any suitable number of sensors can be included and the illustration of two sensors is merely an example. Furthermore, if included, a sensor or sensors can be associated with the plug member in any suitable manner, and the embedded structure illustrated is merely an example. Sensors can also be attached to a surface of the plug member, for example. The inventive medical devices can be used with other medical devices and, indeed, as a component of another medical devices. For example, the medical devices can be used as a wireguide for placement of a delivery system, catheter or other suitable medical device.

Figure 12:
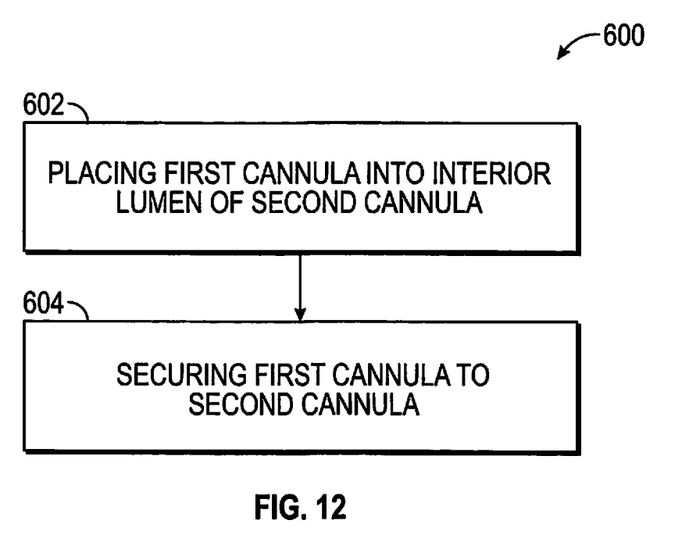
FIG. 12 is a flowchart representation of an example method of making a medical device.

FIG. 12 illustrates an example method 600 of making a medical device. A first step 602 comprises passing a first cannula into an interior lumen of a second cannula that defines a pattern of openings extending along a spiral path on its circumferential wall. A second step 604 comprises securing the first cannula to the second cannula.

While the examples described above reference specific features of particular drawings, it is understood that the various elements and/or features described herein in connection with one particular embodiment can be combined with those of another without departing from the scope of the invention. Furthermore, the cannulae, delivery systems and methods described and illustrated herein are examples. As such, they are not intended to limit the scope of protection sought in any manner. Rather, they serve only to aid those skilled in the art to make apparatuses and to practice methods in accordance with the invention.

We claim:

1. A medical device, comprising:
an outer cannula having an outer cannula lengthwise axis and an outer cannula circumferential wall extending between an outer cannula proximal end and an outer cannula distal end, the outer cannula circumferential wall defining an outer cannula interior lumen and a first side port opening extending through the outer cannula circumferential wall;
an inner cannula disposed within the outer cannula interior lumen and secured to the outer cannula, the inner cannula having an inner cannula lengthwise axis, an inner cannula circumferential wall extending between an inner cannula proximal end and an inner cannula distal end, the inner cannula circumferential wall defining an inner cannula interior lumen, a pattern of openings extending along a spiral path about the inner cannula lengthwise axis, and a second side port opening extending through the inner cannula circumferential wall and aligned with the first side port opening with respect to the inner cannula lengthwise axis;
a side port joint disposed between the outer cannula and the inner cannula and adjacent the second side port opening, the side port joint forming an attachment between the outer cannula and the inner cannula; and
a ramp member disposed within the inner cannula interior lumen and defining a ramp surface aligned with the second side port opening.

2. The medical device of claim 1, wherein the ramp member extends from the second side port opening axially along the inner cannula lengthwise axis and toward the distal end of the inner cannula.

3. The medical device of claim 1, further comprising a distal joint disposed between the outer cannula distal end and the inner cannula distal end, the distal joint forming an attachment between the outer cannula and the inner cannula.

4. The medical device of claim 3, wherein the distal joint comprises a circumferential joint.

5. The medical device of claim 3, wherein the distal joint comprises a joint selected from the group consisting of a weld joint, a brazing joint, and a solder joint.

6. The medical device of claim 1, wherein the side port joint comprises a circumferential joint extending around the second side port opening.

7. The medical device of claim 1, wherein the ramp member extends from the second side port opening axially along the inner cannula lengthwise axis and to the distal end of the inner cannula.

8. The medical device of claim 1, wherein the ramp member extends from the second side port opening axially along the inner cannula lengthwise axis and toward the proximal end of the inner cannula.

9. The medical device of claim 1, wherein the ramp member extends from the second side port opening axially along the inner cannula lengthwise axis and to the proximal end of the inner cannula.

10. The medical device of claim 1, wherein the outer cannula comprises a first metal.

11. The medical device of claim 10, wherein the inner cannula comprises a second, different metal.

12. The medical device of claim 11, wherein the first metal comprises stainless steel and the second metal comprises a superelastic alloy.

13. A medical device, comprising:
an outer cannula having an outer cannula lengthwise axis and an outer cannula circumferential wall extending between an outer cannula proximal end and an outer cannula distal end, the outer cannula circumferential wall defining an outer cannula interior lumen and a first side port opening extending through the outer cannula circumferential wall, the outer cannula comprising a polymeric material and being free of openings in the outer cannula circumferential wall other than the first side port opening;
an inner cannula disposed within the outer cannula interior lumen and secured to the outer cannula, the inner cannula having an inner cannula lengthwise axis, an inner cannula circumferential wall extending between an inner cannula proximal end and an inner cannula distal end, the inner cannula circumferential wall defining an inner cannula interior lumen, a pattern of openings extending along a spiral path about the inner cannula lengthwise axis, and a second side port opening extending through the inner cannula circumferential wall and aligned with the first side port opening with respect to the inner cannula lengthwise axis, the inner cannula comprising a metal;
a side port joint disposed between the outer cannula and the inner cannula, the side port joint comprising a circumferential joint extending around the second side port opening and forming an attachment between the outer cannula and the inner cannula; and
a ramp member disposed within the inner cannula interior lumen and defining a ramp surface aligned with the second side port opening.

14. The medical device of claim 13, further comprising a distal joint disposed between the outer cannula distal end and the inner cannula distal end, the distal joint forming an attachment between the outer cannula and the inner cannula.

15. The medical device of claim 14, wherein the distal joint comprises a circumferential joint.

16. The medical device of claim 14, wherein the distal joint comprises a joint selected from the group consisting of a weld joint, a brazing joint, and a solder joint.

17. The medical device of claim 13, wherein the ramp member extends from the second side port opening axially along the inner cannula lengthwise axis and toward the distal end of the inner cannula.

18. The medical device of claim 13, wherein the ramp member extends from the second side port opening axially along the inner cannula lengthwise axis and to the distal end of the inner cannula.

19. The medical device of claim 13, wherein the ramp member extends from the second side port opening axially along the inner cannula lengthwise axis and toward the proximal end of the inner cannula.

20. The medical device of claim 13, wherein the ramp member extends from the second side port opening axially along the inner cannula lengthwise axis and to the proximal end of the inner cannula.

* * * * *